(12) United States Patent
Xu et al.

(10) Patent No.: US 10,064,794 B2
(45) Date of Patent: Sep. 4, 2018

(54) ORAL CARE COMPOSITION

(71) Applicant: Colgate-Palmolive Company, Piscataway, NJ (US)

(72) Inventors: Yun Xu, Guangzhou (CN); Xiao Yi Huang, Guangzhou (CN); Yuan Hui Xie, Guangzhou (CN); Xiong Fei Qin, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/654,511

(22) PCT Filed: Dec. 24, 2012

(86) PCT No.: PCT/CN2012/087270
§ 371 (c)(1),
(2) Date: Jun. 19, 2015

(87) PCT Pub. No.: WO2014/100928
PCT Pub. Date: Jul. 3, 2014

(65) Prior Publication Data
US 2015/0328094 A1   Nov. 19, 2015

(51) Int. Cl.
| | |
|---|---|
| *A61Q 11/00* | (2006.01) |
| *A61K 8/19* | (2006.01) |
| *A61K 8/27* | (2006.01) |
| *A61K 8/25* | (2006.01) |
| *A61K 33/06* | (2006.01) |
| *A61K 8/365* | (2006.01) |

(52) U.S. Cl.
CPC .............. *A61K 8/19* (2013.01); *A61K 8/25* (2013.01); *A61K 8/27* (2013.01); *A61K 8/365* (2013.01); *A61Q 11/00* (2013.01); *A61K 2800/28* (2013.01); *A61K 2800/592* (2013.01)

(58) Field of Classification Search
CPC ... A61K 8/25; A61K 8/19; A61K 8/27; A61K 8/365; A61K 2800/592; A61K 2800/28; A61Q 11/00
See application file for complete search history.

(56) References Cited

U.S. PATENT DOCUMENTS

| | | | |
|---|---|---|---|
| 5,188,820 A | 2/1993 | Cummins et al. | |
| 6,503,483 B2 | 7/2003 | Shuch et al. | |
| 2009/0010857 A1 | 1/2009 | Waterfield | |
| 2009/0202454 A1* | 8/2009 | Prencipe | A61K 8/19 424/52 |
| 2015/0297500 A1* | 10/2015 | Robinson | A61K 8/27 424/401 |

FOREIGN PATENT DOCUMENTS

| | | |
|---|---|---|
| CN | 102218021 | 10/2011 |
| CN | 102283794 | 12/2011 |
| CN | 102283795 | 12/2011 |
| CN | 102512335 | 6/2012 |
| CN | 102512349 | 6/2012 |
| EP | 2438901 | 11/2012 |
| WO | WO 97/04741 | 2/1997 |
| WO | WO 99/47108 | 9/1999 |
| WO | WO 2004/047784 | 10/2004 |
| WO | WO 2006/050777 | 5/2006 |
| WO | WO 2006/050777 A1 | 5/2006 |
| WO | WO 2007/076396 | 5/2007 |
| WO | WO 2007/076001 | 7/2007 |
| WO | WO 2008/006725 | 1/2008 |
| WO | WO 2008/157033 | 12/2008 |
| WO | WO 2003/100265 | 8/2009 |
| WO | WO 2010/0138492 | * 12/2010 |
| WO | WO 2011/094499 | 4/2011 |
| WO | WO 2011 094505 | 8/2011 |
| WO | WO 2011/123123 A1 | 10/2011 |
| WO | WO 2012/031785 | 3/2012 |
| WO | WO 2012/076310 | 6/2012 |
| WO | WO 2012/087288 A2 | 6/2012 |
| WO | WO 2012/031786 | 3/2017 |

OTHER PUBLICATIONS

International Search Report and Written Opinion for international Application No. PCT/CN2012/087270 dated Oct. 3, 2013.

* cited by examiner

*Primary Examiner* — Lezah Roberts

(57) ABSTRACT

The present invention relates to a tooth whitening oral care composition, the use of abrasives in such an oral care composition, a method of polishing tooth enamel, and an oral care kit comprising the oral care composition.

15 Claims, No Drawings

ORAL CARE COMPOSITION

CROSS-REFERENCE TO RELATED APPLICATIONS

This application is a United States National Stage Application under 35 U.S.C. § 371 of International Application PCTCN2012/087270, filed on Dec. 24, 2012, the contents of which is hereby incorporated by reference in its entirety.

BACKGROUND OF THE INVENTION

Tooth enamel is a porous material. Consequently, it can become discoloured as a result of exposure to coloured materials. Examples of such materials include the pigments produced by oral microbes, and pigments found in foodstuffs, beverages, tobacco products, and medicaments. Discoloured teeth are widely considered to be cosmetically unattractive. There is therefore significant consumer demand for oral care compositions with tooth whitening properties.

A number of methods for whitening teeth are known. Of these, the use of tooth-whitening toothpastes is perhaps the most common; most whitening toothpastes can be administered by consumers without the intervention of a dental professional. Whitening toothpastes typically comprise an abrasive, which polishes the teeth when applied by brushing. The abrasive must be carefully selected. The abrasive must produce a whitening effect without damaging the tooth enamel.

Certain common abrasives, such as calcium carbonate, have relatively low abrasiveness. While they may contribute to the cleaning of teeth, they fail to produce an appreciable whitening effect. In contrast, many silicas are relatively strong abrasives and are desirably incorporated into tooth whitening formulations. Slicas are known to interact with some functional ingredients, particularly metal ions such as zinc (II). Antimicrobial ingredients are useful for the treatment or prevention of other oral diseases or disorders, including dental caries and periodontal disease, and are commonly included in oral care compositions. Since oral bacteria can contribute to tooth discolouration, it is desirable to incorporate antimicrobial ingredients into tooth whitening products.

Zinc compounds are a particularly useful class of antimicrobial ingredients. Zinc has been shown to fight plaque, to prevent the formation of dental calculus, and to reduce mouth malodour. Zinc can also aid in the treatment and prevention of tooth hypersensitivity. While zinc offers many oral health benefits, its organoleptic characteristics are poor. It is therefore desirable to reduce the levels of zinc used in oral care compositions, while still providing oral health benefits. This would improve consumer acceptance of oral care compositions comprising zinc. A further aim is to provide a tooth whitening composition comprising a reduced concentration of zinc while maintaining high antimicrobial efficacy.

In a first aspect, the present invention provides a dentifrice comprising zinc compounds and abrasives, wherein the abrasives comprises abrasive silica and calcium carbonate, and wherein the composition is a tooth whitening and enamel strengthening composition.

Optionally, the pH of the composition is at least 7.0.

Optionally, the pH of the composition is in the range pH 9.4 to 10.0.

Optionally, the abrasive is present in an amount in the range 10% to 45% by weight of the composition.

Optionally, the abrasive is present in an amount in the range 25% to 45% by weight of the composition.

Optionally, the zinc compound is present in the composition in an amount in the range of about 0.1 wt % to about 5 wt % by weight of the composition. The amount of zinc ions in the specification can also be characterized by the corresponding percentage weight of the zinc ions relative to the zinc compound (e.g. about 0.1 wt % to about 5 wt % of zinc oxide corresponds to about 0.08 wt % to 4.02 wt % of zinc ions).

Optionally, the calcium carbonate comprises natural calcium carbonate.

Optionally, the calcium carbonate is present in an amount in the range 10% to 35% by weight of the composition.

Optionally, the abrasive silica comprises silica with a mass median diameter in the range 3 to 4 μm.

Optionally, the abrasive silica is present in an amount in the range 3% to 25% by weight of the composition.

Optionally, the composition thither comprises at least one additional ingredient selected from the group consisting of surfactants, desensitising agents, whitening agents, tartar control agents, binders, thickening agents, detergents, adhesion agents, foam modulators, pH modifying agents, mouth feel agents, sweeteners, flavourants, colourants, preservatives, humectants, fluoride sources and combinations thereof.

In a second aspect, the invention provides an oral care kit comprising the dentifrice composition.

In a third aspect, the invention provides the use of the composition in tooth whitening.

In a fourth aspect, the invention provides a method of polishing tooth enamel comprising applying the composition to the surface of the enamel.

It has surprisingly been found that, by incorporating calcium carbonate into a tooth whitening composition based on abrasive silica it was possible to increase zinc uptake. This enables enhanced antibacterial, anticavity, enamel erosion protection, breath fresheners and other benefits in tooth-whitening compositions.

DETAILED DESCRIPTION OF THE INVENTION

It should be understood that the detailed description and specific examples, whilst indicating embodiments of the invention, are intended for the purpose of illustration only and are not intended to limit the scope of the invention.

As used throughout, ranges are used as shorthand for describing each and every value that it is within the range. Any value within the range can be selected as the terminus of the range.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a composition or method of this invention, indicates that the calculation or the measurement of the value allows some slight imprecision without having a substantial effect on the chemical or physical attributes of the composition or the method. If, for some reason, the imprecision provided by "about" is not otherwise understood in the art with this ordinary meaning, then "about" as used herein indicates a possible variation of up to 5% in the value.

As referred to herein, compositional percentages are by weight of the total composition, unless otherwise specified.

As used herein, "ppm" (parts per million) refers to ppm by weight, unless otherwise indicated.

As referred to herein, all ratios refer to weight ratios, unless otherwise indicated.

The dentifrice composition of the present invention comprises at least one zinc compound and an abrasive. The abrasive comprises abrasive silica and calcium carbonate. The composition is a tooth whitening composition.

The zinc compound may function as an antimicrobial ingredient and/or provide oral health benefits when the composition is used as a dentifrice. Examples of oral health benefits include the prevention of mouth malodour and enamel erosion, and the treatment or prevention of oral diseases such as dental caries, periodontal diseases and tooth hypersensitivity. It is believed that zinc can permeate tooth enamel during use of the composition. The adsorbed zinc may be gradually released into the saliva of the subject over time, for example, over a period of at least 8 hours or at least 12 hours. The compositions of the invention may therefore provide sustained oral health benefits.

The compositions of the present invention comprise an abrasive. The abrasive provides a cleaning effect and preferably a tooth whitening effect. The abrasive comprises abrasive silica and calcium carbonate. Typically, the calcium carbonate and silica selected will not cause permanent damage to tooth enamel during normal use of the composition.

Abrasive silica is a relatively strong abrasive. Typically, the abrasive silica produces a tooth whitening effect. Abrasive silicas are distinct from thickening silicas. In general, abrasive (cleaning) silicas can be characterized as having oil absorption levels of about 40 to 150 cc/100 g and having an Einlehner abrasion of 3 or greater mg loss/100,000 revolutions whereas thickening abrasives have oil absorption levels of greater than 150 cc/100 g and having an Einlehner abrasion of less than 2 mg loss/100,000 revolutions.

The abrasive silica is optionally a precipitated or hydrated silica having a mean particle size of up to about 20 microns, such as Zeodent 103, 105, 113, 114, 115, or 124 marketed by J.M. Huber Chemicals Division, Havre de Grace, Md. 21078, or Sylodent 783 marketed by Davison Chemical Division of W.R. Grace & Company. Other possible abrasive silicas include silica gels and precipitated amorphous silica having an oil adsorption value of less than 100 cc/100 g silica and optionally in the range of from about 45 cc/100 g to less than about 70 cc/100 g silica. These silicas are colloidal particles having an average particle size ranging from about 3 microns to about 12 microns, and optionally between about 5 to about 10 microns.

Thickening abrasives can include silicas such as Zeodent 163 (oil absorption levels of 190 cc/100 g and having an Einlehner abrasion of less than 2 mg loss/100,000 revolutions), Zeodent 165 (oil absorption levels of 220 cc/100 g and having an Einlehner abrasion of less than 2 mg loss/100,000 revolutions), Zeodent 167 (oil absorption levels of 235 cc/100 g and having an Einlehner abrasion of less than 2 mg loss/100,000 revolutions) marketed by J.M. Huber Chemicals Division, Havre de Grace, Md. 21078. When used alone, silica may greatly inhibits the uptake of zinc by tooth enamel. Calcium carbonate is found to mitigate this effect. Typically, calcium carbonate is itself a mild abrasive and will contribute to the cleaning action of the composition. Some forms of calcium carbonate are not sufficiently abrasive to provide a significant tooth whitening effect when used alone.

A tooth whitening composition is a composition which is capable of reducing the discolouration of teeth. A tooth whitening composition may preferably restore the natural colour of the teeth. Optionally, a tooth whitening composition may reduce or eliminate stains. Multiple applications of a tooth-whitening composition may be needed to produce a discernible effect. Preferably, the tooth whitening effect is discernible after the first use of the composition.

The dentifrice compositions of the present invention preferably have a pH of at least about 7.0; pH values in this range enhance the uptake of zinc from compositions comprising calcium carbonate and silica. The pH of the composition will typically be less than or equal to the maximum pH of about 10.0 which can be tolerated in oral care compositions. The composition may optionally comprise at least one pH adjusting and/or pH buffering agent in an effective amount to adjust the pH of the composition to the target value.

The pH of a dentifrice composition may be determined by preparing a slurry comprising 10% w/w of the dentifrice and 90% w/w of deionised water. To avoid systematic errors caused by dissolved carbon dioxide, the deionised water is preferably degassed before use and measurements are preferably performed in an inert gas atmosphere. The pH of the slurry may be measured using any technique known in the art, for example by using a glass electrode and electronic pH meter.

Optionally, the pH of the oral care compositions of the invention will be at least 8, or at least 9, or greater than 9.5. Preferably, the pH of the compositions is between pH 9.0 and pH 10.0. More preferably, the pH of the compositions is between pH 9.4 and pH 10.0, for example greater than pH 9.5 to pH 10.0. Optionally, the pH of the composition is about pH 9.0, or about pH 9.1, or about pH 9.3, or about 9.5, or about pH 9.5, or about pH 9.7, or about pH 9.8.

Typically, the compositions of the invention will comprise an effective amount of abrasive so as to provide a stain removal, tooth whitening and/or cleaning effect. Preferably, the abrasive is present in the composition in an amount in the range 10% to 45% by weight of the composition. More preferably, the abrasive is present in the composition in an amount in the range 25% to 45% by weight of the composition. Optionally, the total amount of abrasive is about 15%, or about 20% or about 25%, or about 30%, or about 35%, or about 40%, or about 42% by weight of the composition. Most preferably, the total amount of abrasive present in the composition is about 40% by weight of the composition.

Typically, the zinc compound will be present in the composition in an amount which is effective to deliver an oral health benefit. The amount of zinc present in the composition will typically be less than the level which would cause excessive adverse effects. In general, the dosage of zinc may be selected so as to achieve an acceptable benefit/risk ratio. Preferably, the zinc is not organoleptically discernible by the average consumer.

Optionally, the zinc is present in an amount in the range 0.1% to 5% by weight of the composition. In one embodiment of the invention, the zinc is present in the form of a zinc compound. Preferably, the zinc compound is present in an amount in the range 0.2% to 3% by weight of the composition, such as 0.5 to 2% or 1 to 3%. Optionally, the zinc compound is present in the composition in an amount of about 0.5%, or about 1%, or about 1.5%, or about 2%, or about 2.5%, or about 3% by weight of the composition.

Preferably, the zinc compound is present in the composition in an amount of about 1.5% by weight of the composition.

Any zinc compound which is suitable for use in an oral care composition may be used in the compositions of the present invention. In one embodiment of the invention, the zinc compound is selected from the group consisting of zinc acetate, zinc borate, zinc butyrate, zinc carbonate, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof. In one embodiment of the invention, the zinc compound is selected from the group consisting of zinc oxide, zinc citrate, and mixtures thereof.

In another embodiment of the invention, the zinc compound comprises a mixture of zinc compounds. Where there is a mixture of two zinc compounds the weight ratio of the compounds may be in a range selected from the group consisting of from about 1:4 to about 6:1, about 1:3 to about 5:1 and about 1:2 to about 4:1.

In another embodiment where the zinc compound is a mixture of zinc compounds, the mixture is of zinc citrate and zinc oxide. In an embodiment of this aspect of the invention, the amount zinc citrate is selected from the range consisting of about 0.25 wt % to about 2.5 wt % and about 0.5 wt % to about 2 wt % and the amount of zinc oxide is selected from the range consisting of about 0.25 wt % to about 1.5 wt % and about 0.5 wt % to about 1 wt %. Preferably, the composition comprises a weight ratio of zinc citrate:zinc oxide of about 1:2, and preferably comprises about 0.5% zinc citrate and about 1% zinc oxide by weight of the composition.

Preferably, the calcium carbonate comprises natural calcium carbonate (NCC). Natural calcium carbonate is typically obtained by cleaning and milling natural materials such as limestone, sea shells and the like. Preferably, the natural calcium carbonate has ≥99.5 wt % passing 400 mesh sieve and ≥99.9 wt % passing 325 mesh sieve (both calculated by manual wet method LAB-2256).

The calcium carbonate used in the compositions of the invention may optionally be precipitated calcium carbonate.

The calcium carbonate will be present in the composition in an amount which is sufficient to provide enhanced uptake of zinc. The calcium carbonate is preferably present in an amount which provides a cleaning benefit.

Preferably, the calcium carbonate is present in the composition in the amount in the range 10% to 35% by weight of the composition. More preferably, the calcium carbonate is present in the composition in an amount in the range 25% to 35% by weight of the composition. Optionally, the calcium carbonate is present in the composition in an amount of about 10% or about 15%, or about 20% or about 30% or about 35% by weight of the composition.

The compositions of the present invention also include an abrasive silica. The abrasive silica is optionally precipitated or hydrated silica having a mean particle size of up to about 20 microns, such as Zeodent 103, 105, 113, 114, 115, or 124 marketed by J.M. Huber Chemicals Division, Havre de Grace, Md. 21078, or Sylodent 783 marketed by Davison Chemical Division of W.R. Grace & Company. Other possible abrasive silicas include silica gels and precipitated amorphous silica having an oil adsorption value of less than 100 cc/100 g silica and optionally in the range of from about 45 cc/100 g to less than about 70 cc/100 g silica. These silicas are colloidal particles having an average particle size ranging from about 3 microns to about 12 microns, and optionally between about 5 to about 10 microns or between about 3 to about 4 microns (e.g. AC43).

Typically, the silica may be present in the composition in an amount which is effective to produce a tooth whitening and/or cleaning effect. The amount of silica will generally be selected so as to avoid excessive abrasion of the tooth surface. The abrasiveness of a composition may be measured using, for example, the radioactive dentine abrasion test method or other methods known in the art.

Preferably, the abrasive silica is present in an amount in the range about 5% to about 25% by weight of the composition. More preferably, the abrasive silica is present in an amount in the range about 10% to about 20% by weight of the composition. Most preferably, the abrasive silica is present in an amount of about 15% by weight of the composition.

The weight ratio of calcium carbonate to abrasive silica will be selected so as to provide the desired level of abrasiveness and the desired level of zinc uptake. Preferably, the weight ratio of the amount of calcium carbonate to the amount of abrasive silica is in the range selected from the group consisting of about 1:2 to about 2:1, about 1:2 to about 2:1, about 3:4 to about 4:3, about 5:6 to about 6:5, about 9:10 to about 10:9 and about 1:1.

The compositions of the present invention may comprise one or more additional oral care ingredients. The one or more additional oral care ingredients may optionally be selected from the group consisting of: surfactants, desensitising agents, whitening agents, tartar control agents, binders, thickeners, detergents, adhesion agents, foam modulators, pH modifying agents, mouth feel agents, sweeteners, flavourants, colourants, preservatives, humectants, fluoride sources and combinations thereof.

Surfactants may be used in the oral care compositions of the present invention to provide foaming, taste, flavour, texture and mouth feel properties to the compositions, and in particular to render the compositions more cosmetically acceptable. Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine. Preferably, the surfactant comprises sodium lauryl sulfate (SLS).

The composition of the present invention optionally incorporates one or more desensitizing agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt. % to about 20 wt. % by weight based on the total weight of the composition, depending on the agent chosen. The compositions of the present invention may also be used to treat hypersensitivity by blocking dentin tubules when applied to a tooth.

The compositions of the present invention may optionally include a tooth whitening or tooth bleaching agent. Suitable whitening and bleaching agents include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include per-borate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1 wt. % to about 20 wt. % by weight based on the total weight of the composition, depending on the agent chosen.

The oral care compositions of the present invention may optionally include tartar control agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ sodium tripolyphosphate, long chain polyphosphates such as sodium hexametaphosphate and cyclic phosphates such as sodium trimetaphosphate.

The compositions of the invention may contain a binder. Any conventional binder may be utilized. Suitable agents include marine colloids; carboxyvinyl polymers; carrageenans; starches; cellulosic polymers such as hydroxyethylcellulose. carboxymethylcellulose (cannellose), hydroxypropyl methyl cellulose, and salts thereof (e.g., cannellose sodium); natural gums such as karaya, xanthan, gum arabic and tragacanth; chitosan; colloidal magnesium aluminum silicate; and colloidal silica. Preferably, a binder is present in the composition in an amount in the range about 0.5% to about 5% by weight of the composition.

Thickening agents suitable for use in the compositions of the present invention include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds which function as thickening agents and include colloidal silicas compounds available under the trade designation Cab-o-sil manufactured by Cabot Corporation and distributed by Lenape Chemical, Bound Brook, N.J., Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickening agents include natural and synthetic clays such as hectorite clays, lithium magnesium silicate (laponite) and magnesium aluminum silicate (Veegum).

The oral care compositions of the present invention may optionally comprise one or more adhesion agents. The adhesion agent may by a polymeric adherent material. The polymeric adherent material may be any known or to be developed in the art that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylinethyl cellulose (HPMC), hydroxyethylpropyl cellulose (HEPC), hydroxybutylinethyl cellulose (HBMC), carboxymethyl cellulose (CMC).

Preferably, the polymeric adherent material comprises at least one cellulose material, for example sodium carboxymethyl cellulose.

The polymeric adherent material may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). Optionally, the copolymer may be selected from the group consisting of: poly (methylvinylether/maleic anhydride), or poly (methylvinylether/maleic acid), or poly (methylvinylether/maleic acid) half esters, or poly (methylvinylether/maleic acid) mixed salts.

Polymers of any molecular weight may be used, including, for example molecular weights of 50,000 to 500,000, 500,000 to 2,500,000 or 2,500,000 to Ser. No. 10/000,000 (calculated by either number average or weight average).

The oral care compositions of the invention also may include a foam modulator. Foam modulators typically increase the amount of foam produced, for example, when the oral cavity is brushed using the composition of the present invention.

Illustrative examples of foam modulators that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000, and preferably about 600,000 to about 2,000,000 and more preferably about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The foaming agent is preferably in the oral care composition in an amount in the range about 0.01 to about 0.9%, or about 0.05 to about 0.5%, or about 0.1 to about 0.2% by weight of the composition.

Preferably, the compositions of the present invention comprise at least one pH modifying agent. Such agents include acidifying agents to lower pH, basifying agents to raise pH, and buffering agents to control pH within a desired range. The pH modifying agent preferably comprises a basifying agent and/or a buffering agent. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used including, without limitation, carboxylic, phosphoric and sulfonic acids, acid salts (e.g., monosodium citrate, disodium citrate, monosodium malate, etc.); alkali metal hydroxides such as sodium hydroxide; carbonates such as sodium carbonate, bicarbonates, sesquicarbonates; borates; silicates; phosphates (e.g., monosodium phosphate, trisodium phosphate, pyrophosphate salts, etc.), imidazole and the like. One or more pH modifying agents are preferably present in a total amount effective to maintain the composition in an orally acceptable pH range.

Mouth-feel agents that may be used herein include materials which impart a desirable texture or other feeling during use of the composition. Such agents include bicarbonate salts, which may impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate, and mixtures thereof. One or more bicarbonate salts are optionally present in a total amount of 0.1% to about 50%, for example about 1% to about 20% by weight.

The compositions of the present invention may optionally comprise a sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol. These may be present in amounts of 0 wt % to 0.2 wt %, optionally 0.005 wt % to 0.1 wt % based on the weight of the composition.

The compositions of the present invention may optionally comprise a flavourant. Flavourants that may be used in the compositions of the present invention include essential oils as well as various flavoring aldehydes, esters, alcohols, and similar materials. Examples of the essential oils include oils of spearmint, peppermint, aniseed, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The flavourant may be incorporated in the composition at a concentration into the range 0.1 to 5 wt % or 0.5 to 1.5 wt %.

A composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

Preservatives, such as chlorhexidine, triclosan, quaternary ammonium compounds (such as benzalkonium chloride) or parabens (such as methyl or propyl paraben) may be used in the compositions. The amount of preservative is typically in the range from 0 to about 0.5 wt %, optionally 0.05 to 0.1 wt % based on the weight of the composition.

The compositions of the present invention may optionally comprise a humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount in the range of from about 1 wt. % to about 70 wt. %, for example, from about 1 wt. % to about 50 wt. %, from about 2 wt. % to about 25 wt. %, or from about 5 wt. % to about 15 wt. %, by total weight of the composition.

Preferably, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. Optionally, the fluoride ion source includes stannous fluoride, sodium fluoride, amine fluorides, sodium monofluorophosphate, as well as mixtures thereof. Preferably, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level in the range of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

Also provided is a method of treating or preventing a disease or disorder of the oral cavity in a human or animal subject, which method comprises applying the oral care composition as defined herein to the oral cavity of the subject.

Preferably, the subject is a human, or a companion animal such as a cat, a dog or a horse. Most preferably, the subject is a human. The composition may be applied by the any suitable method known in the art. The composition may be applied to the oral cavity of the subject using any suitable technique known in the art. The technique may vary depending on the nature of the composition. For example, the composition is preferably applied by brushing and more preferably by brushing for about 2 minutes.

Any appropriate dosage regime may be used in combination with the method of the present invention. For example, the composition may be applied to the oral cavity of the subject once a day, twice a day, or more often. Preferably, the composition is applied to the oral cavity of the subject twice a day. The subject may be treated with the composition for a period of at least one day, at least one month, at least six months, at least one year, or for a lifetime.

Various diseases and disorders of the oral cavity may be treated or prevented using the methods and compositions of the present invention. Optionally, the methods and compositions of the present invention may be used to treat or prevent a chronic disease or disorder. The disease or disorder could be dental caries. The disease or disorder may be a periodontal disease, or periodontal inflammation. The periodontal disease may be gingivitis. The disease or disorder may be halitosis.

The disease or disorder may be tooth hypersensitivity. If the disease or disorder is tooth hypersensitivity, the composition preferably comprises an additional oral care ingredient which is a desensitizing agent. The disease or disorder may be the buildup of tartar and/or calculus formation. If the disease or disorder is the buildup of tartar and/or calculus formation, the composition preferably comprises an additional oral care ingredient which is a tartar control agent.

A further aspect of the present invention provides an oral care kit comprising the oral care composition described above. The kits of the present invention preferably comprise the composition of the invention disposed in appropriate packaging. The kits of the invention may optionally comprise a suitable applicator, such as a toothbrush or the like. The kits of the invention may optionally comprise means for measuring an appropriate dosage the composition.

Another aspect of the present invention provides a method of polishing tooth enamel. The method comprises applying the composition of the invention to the surface of the enamel. Preferably, the composition is applied in a slurry comprising the composition and a continuous liquid phase, preferably wherein the liquid phase is water. Typically, the composition is applied by brushing. Preferably, the composition is applied by brushing for at least 2 minutes using a manual or mechanical toothbrush. Most preferably, the method of polishing tooth enamel is a method of whitening teeth.

Still another aspect of the present invention provides the use of the composition described herein in tooth whitening.

Specific Embodiments of the Invention

The invention is thither described in the following Examples. The Examples are merely illustrative and do not in any way limit the scope of the invention as described and claimed. This invention can be further illustrated by the following Examples of preferred embodiments thereof, although it will be understood that these Examples are included merely for purposes of illustration and are not intended to limit the scope of the invention unless otherwise specifically indicated.

EXAMPLES

Example 1: Dentifrice Compositions

Dentifrice compositions of the invention and comparative dentifrice compositions were produced according to the present invention. The uptake of zinc into hydroxyapatite discs treated with each of the formulations was determined.

Materials and Methods

Dentifrice compositions comprising the ingredients set out in the table below were prepared according to standard methods. The pH of slurries of each composition and the uptake of zinc from each of the compositions was then determined using the methods described in Example 2, below.

| | Formulation | | | | | |
|---|---|---|---|---|---|---|
| Ingredient | Comp. formula 1 Amount % w/w | Comp. formula 2 Amount % w/w | Comp. formula 3 Amount % w/w | Formula 1 Amount % w/w | Formula 2 Amount % w/w | Formula 3 Amount % w/w |
| Water | 25.59 | 32.59 | 15.39 | 27.59 | 27.59 | 27.59 |
| Sorbitol - 70% solution | 21.00 | 21.00 | 55.00 | 21.00 | 21.00 | 21.00 |
| Sodium saccharin | 0.35 | 0.35 | 0.30 | 0.35 | 0.35 | 0.35 |
| Tetrasodium pyrophosphate (TSPP) | 1.00 | 1.00 | 1.00 | 1.00 | 1.00 | 1.00 |
| Sodium bicarbonate | 1.00 | 1.00 | | 1.00 | 1.00 | 1.00 |
| Tetrapotassium pyrophospate (TKPP) | 1.00 | 1.00 | 1.00 | 1.00 | 1.00 | 1.00 |
| Carboxymethyl-cellulose (CMC) | 0.75 | 0.75 | 0.80 | 0.75 | 0.75 | 0.75 |
| Xanthan gum | 0.30 | 0.30 | 0.30 | 0.30 | 0.30 | 0.30 |
| Monofluorophosphate | 0.76 | 0.76 | 0.76 | 0.76 | 0.76 | 0.76 |
| Natural calcium carbonate (NCC) | 42.00 | 35.00 | | 35.00 | 25.00 | 15.00 |
| Abrasive silica (Zeo 114) | | | 10.00 | | 15.00 | 25.00 |
| Thickening silica (DT 267) | 0.50 | 0.50 | 4.00 | 0.50 | 0.50 | 0.50 |
| Abrasive silica (AC43) | | | 5.00 | 5.00 | | |
| Zinc oxide | 1.00 | 1.00 | 1.00 | 1.00 | 1.00 | 1.00 |
| Zinc citrate | 0.50 | 0.50 | 0.50 | 0.50 | 0.50 | 0.50 |
| Betaine | | | 1.25 | | | |
| Titanium dioxide | 0.75 | 0.75 | 0.50 | 0.75 | 0.75 | 0.75 |
| Sodium lauryl sulphate | 2.00 | 2.00 | 2.00 | 2.00 | 2.00 | 2.00 |
| Benzyl alcohol | 0.30 | 0.30 | | 0.30 | 0.30 | 0.30 |
| Flavor | 1.20 | 1.20 | 1.20 | 1.20 | 1.20 | 1.20 |

Example 2: The Effect of Various Abrasives on Zinc Uptake

The effects of silica, natural calcium carbonate, and mixtures thereof on the uptake of zinc by hydroxyapatite discs were investigated. Natural calcium carbonate was found to enhance the uptake of zinc. Silica reduced the uptake of zinc.

Materials and Methods

Dentifrice compositions comprising 1% w/w zinc oxide and 0.5% w/w zinc citrate and varying amounts of silica and natural calcium carbonate were prepared according to a standard method. The amount of silica varied from 0% to 25%. The amount of natural calcium carbonate varied from 0% to 42%.

Slurries consisting of 90% w/w degassed deionised water and 10% of the dentifrice were prepared. The natural pH of the slurries was then recorded using a glass combination electrode and an electronic pH meter. The day before testing, sufficient saliva is obtained to cover the amount of HAP discs to be used. For example, 30 mLs for 30 mls (1 ml for each disc). The saliva is centrifuged to remove particulates. (8,000 rpm for 10 min). One disc in placed in a Falcon® tube (conical round bottomed tube) and 1 mL of saliva is added. The tube is incubated overnight in the 37 degree water bath. On the next day, toothpaste slurries are prepared in plastic white covered jars. The slurries are made in a 1:2 dilution. (10 g of paste with 20 g of water). To mix, a speed mixer is used for 2 min. The slurries in the jars are then placed on a stir plate to keep them mixing. The saliva is subsequently removed by vacuum. 1 mL of slurry is added and vortexed for 5 seconds for each sample. The mixture is then permitted to sit for 15 min. The slurry is removed and the HAP disk is rinsed with 1 ml DI water, 2 times. The pipet tip is changed after each toothpaste. The HAP disc is placed in 50 mL purple top tube and 20 mL of 10% nitric acid is added. The HAP disc is then permitted to dissolve completely (app. 2 hours). The tube is then centrifuged at 8,000 rpm for 10 min. The supernatant (10 mL) is placed in 15 mL purple top Falcon tube and analyzed for total zinc content.

Results and Discussion

1. Natural Calcium Carbonate Alone

Table 1 show the data collected for a series of dentifrices comprising 0% silica and varying amounts of natural calcium carbonate.

TABLE 1

| Amount of calcium carbonate/% | Amount of silica/% | Total amount of zinc by wt % of composition | pH of slurry | Amount of soluble zinc by wt % of composition | Average zinc uptake (ppm/disk) |
|---|---|---|---|---|---|
| 0 | 0 | 0.96 | 9.67 | 0.28 | 267 |
| 10 | 0 | 0.96 | 9.73 | 0.24 | 277 |
| 15 | 0 | 0.96 | 9.78 | 0.29 | 256 |
| 25 | 0 | 0.96 | 9.87 | 0.25 | 271 |
| 35 | 0 | 0.96 | 9.74 | 0.26 | 291 |
| 42 | 0 | 0.96 | 9.78 | 0.25 | 291 |

The pH values for the slurries varied by a maximum of 0.2 pH units. It is believed that this small variation would not significantly impact the uptake of zinc by the hydroxyapatite discs; the amounts of soluble zinc present in the dentifrice compositions investigated did not vary significantly.

The data show that the inclusion of calcium carbonate alone, regardless of amount, in a dentifrice composition results in no significant change in the amount of zinc adsorbed by hydroxyapatite.

2. Silica Alone

Table 2 shows the impact of silica on zinc uptake in a composition comprising no natural calcium carbonate.

TABLE 2

| Amount of calcium carbonate/% | Amount of silica/% | Total amount of zinc by wt % of composition | pH of slurry | Amount of soluble zinc by wt % of composition | Average zinc uptake (ppm/disk) |
|---|---|---|---|---|---|
| 0 | 0 | 0.96 | 9.67 | 0.28 | 267 |
| 0 | 10 | 0.96 | 9.51 | 0.28 | 209 |
| 0 | 15 | 0.96 | 9.46 | 0.27 | 184 |

TABLE 2-continued

| Amount of calcium carbonate/% | Amount of silica/% | Total amount of zinc by wt % of composition | pH of slurry | Amount of soluble zinc by wt % of composition | Average zinc uptake (ppm/disk) |
|---|---|---|---|---|---|
| 0 | 10 + 5 (AC43) | 0.96 | 9.32 | 0.23 | 186 |
| 0 | 25 | 0.96 | 9.05 | 0.25 | 118 |

The small variations in pH and the amount of dissolved zinc are not believed to be significant. Moreover, the change in types of silica does not significantly affect the zinc uptake. The data shows a clear negative correlation ($R^2=0.9976$) between the amount of silica present in the dentifrice and the amount of zinc adsorbed.

3. Mixtures of Silica and Calcium Carbonate

Table 3 shows the impact of increasing levels of natural calcium carbonate in a series of dentifrice compositions comprising 12% silica.

TABLE 3

| Amount of calcium carbonate/% | Amount of silica/% | Total amount of zinc by wt % of composition | pH of slurry | Amount of soluble zinc by wt % of composition | Average zinc uptake (ppm/disk) |
|---|---|---|---|---|---|
| 0 | 12 | 0.96 | 9.48 | 0.29 | 203 |
| 10 | 12 | 0.96 | 9.58 | 0.27 | 211 |
| 20 | 12 | 0.96 | 9.63 | 0.25 | 236 |
| 30 | 12 | 0.96 | 9.58 | 0.25 | 217 |
| 35 | 12 | 0.96 | 9.63 | 0.24 | 247 |

Again, the pH of the slurries formed by the compositions and the dissolved zinc content of the compositions did not vary significantly. The compositions comprising natural calcium carbonate (NCC) with 12% silica produced little variance in zinc uptake despite the increasing amounts of NCC.

Table 4 shows the impact of increasing levels of silica in a series of dentifrice compositions comprising 15% natural calcium carbonate (NCC).

TABLE 4

| Amount of calcium carbonate/% | Amount of silica/% | Total amount of zinc by wt % of composition | pH of slurry | Amount of soluble zinc by wt % of composition | Average zinc uptake (ppm/disk) |
|---|---|---|---|---|---|
| 15 | 0 | 0.96 | 9.78 | 0.24 | |
| 15 | 5 | 0.96 | 9.59 | 0.21 | 229 |
| 15 | 5 (AC43) | 0.96 | 9.44 | 0.22 | 204 |
| 15 | 10 | 0.96 | 9.53 | 0.25 | 214 |
| 15 | 15 | 0.96 | 9.50 | 0.22 | 205 |
| 15 | 20 | 0.96 | 9.43 | 0.22 | 152 |
| 15 | 25 | 0.96 | 9.34 | 0.20 | 144 |

Example 3: Effect of pH on Zinc Uptake

In the absence of any abrasive materials, the uptake of zinc by hydroxyapatite discs was found to decrease slightly with increasing pH. Surprisingly, in compositions comprising a mixture of calcium carbonate and silica abrasives, the uptake of zinc increased with increasing pH.

Materials and Methods

A dentifrice composition comprising 15% silica and 15% natural calcium carbonate was prepared. A control composition comprising no abrasives was also prepared. Slurries comprising 10% w/w of the composition and 90% w/w degassed deionised water. Samples of the slurries were adjusted to specific pH values using either 0.85% aqueous phosphoric acid or 1% aqueous sodium hydroxide, as appropriate (other acids or bases can also be used to adjust pH). The pH values were recorded using an electronic pH meter and glass combination electrode. The pH of the samples varied from 8.8 to 9.9. The test slurries were applied to hydroxyapatite discs according to the protocol described above a standard procedure The zinc uptake by the hydroxyapatite discs was then determined.

Results and Discussion

Table 5 show the zinc uptake of hydroxyapatite discs exposed to slurries of the control composition at various pH values.

TABLE 5

| % NCC | % silica | pH of 10% slurry | Total amount of zinc by wt % of composition | Average zinc uptake (ppm/disc) |
| --- | --- | --- | --- | --- |
| 0 | 0 | 9.07 | 0.96 | 270 |
| 0 | 0 | 9.27 | 0.96 | 271 |
| 0 | 0 | 9.46 | 0.96 | 269 |
| 0 | 0 | 9.70 | 0.96 | 267 |
| 0 | 0 | 9.88 | 0.96 | 253 |

The data in Table 5 show that in the absence of abrasives the pH does not affect zinc uptake.

Table 6 show the zinc uptake of hydroxyapatite discs exposed to slurries of dentifrice compositions comprising calcium carbonate and silica.

TABLE 6

| % NCC | % silica | pH of 10% slurry | Total amount of zinc by wt % of composition | Average zinc uptake (ppm/disc) |
| --- | --- | --- | --- | --- |
| 15 | 15 | 8.78 | 0.96 | 209 |
| 15 | 15 | 9.08 | 0.96 | 213 |
| 15 | 15 | 9.30 | 0.96 | 216 |
| 15 | 15 | 9.51 | 0.96 | 255 |
| 15 | 15 | 9.71 | 0.96 | 261 |

In contrast to the data from Table 5, the data in Table 6 shows that in the present of abrasive, increasing pH increases zinc uptake.

Surprisingly, the uptake of zinc by hydroxyapatite discs from the compositions comprising a mixture of silica and calcium carbonate was found to increase with pH. Toward the upper limit of the pH range investigated, the uptake of zinc was approximately equal to that of the control. At higher pH, zinc uptake would therefore exceed that of the control. It is believed that these effects would be observed for any composition comprising sufficient amounts of silica and calcium carbonate.

The compositions of the invention therefore surprisingly allow for the simultaneous combination of a zinc compound with a silica abrasive, which would have been expected to bind to the zinc in alkaline pH, when there is a specific combination of a zinc compound, silica abrasive and calcium carbonate. This composition surprisingly allows for the simultaneous whitening of the teeth via the use of the silica abrasive and strengthening of the enamel via the uptake of zinc into the enamel.

The invention claimed is:

1. A dentifrice composition comprising a zinc compound and an abrasive, wherein the abrasive comprises abrasive silica and calcium carbonate, and wherein the composition whitens the teeth and strengthens the enamel; and wherein the zinc compound is present in an amount in the range of 0.1 wt % to 5 wt % and is a mixture of two zinc compounds wherein the weight ratio of the compounds is from 1:4 to 6:1; and the weight ratio of the calcium carbonate to the amount of abrasive silica is in the range of 1:2 to 2:1; and wherein the pH of the dentifrice composition, as measured in a slurry of 10% of the dentifrice composition and 90% of water by weight, is in the range pH 9.4 to pH 10.0;

and wherein the uptake of zinc is increased relative to the same composition having a pH less than 9.4.

2. The composition of claim 1, wherein the abrasive is present in an amount in the range 10% to 45% of the composition by weight of the composition.

3. The composition of claim 2, wherein the abrasive is present in an amount in the range 25% to 45% by weight of the composition.

4. The composition of claim 1, wherein the zinc compound is present in an amount in the range selected from the group consisting of 0.2 wt. % to 3 wt. %, and 0.5 wt. % to 2 wt. %.

5. The composition of claim 1, wherein the zinc compound is selected from the group consisting of zinc acetate, zinc borate, zinc butyrate, zinc carbonate, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof.

6. The composition of claim 1, wherein the zinc compound is a mixture of two zinc compounds wherein the weight ratio of the compounds may be in a range selected from the group consisting of from 1:3 to 5:1 and 1:2 to 4:1.

7. The composition of claim 1 wherein the mixture of two zinc compounds is zinc citrate and zinc oxide in a weight ratio of 1:2 to 4:1.

8. The composition claim 1, wherein the calcium carbonate comprises natural calcium carbonate.

9. The composition of claim 1 wherein the calcium carbonate is present in an amount in the range 25% to 35% by weight of the composition.

10. The composition of claim 1 wherein the abrasive silica is present in an amount in the range 3% to 25% by weight of the composition.

11. The composition of claim 1 wherein the silica comprises a silica with an oil absorption level of about 40 to 50 cc/100 g and having an Einlehner abrasion of 3 or greater mg loss/100,000 revolutions.

12. The composition of claim 1 wherein the weight ratio of the amount of calcium carbonate to the amount of abrasive silica is in the range selected from the group consisting of 3:4 to 4:3, 5:6 to 6:5, 9:10 to 10:9, and 1:1.

13. The composition of claim 1 further comprising al least one additional ingredient selected from the group consisting of; surfactants, desensitizing agents, whitening agents, tartar control agents, binders, thickening agents, detergents, adhesion agents, foam modulators, pH modifying agents, mouth feel agents, sweeteners, flavourants, colourants, preservatives, humectants, fluoride sources and combinations thereof.

14. An oral care kit comprising the composition of claim 1.

15. A method of polishing and whitening the teeth and strengthening the tooth enamel, comprising applying the composition of claim 1 to the surface of the enamel.

\* \* \* \* \*